United States Patent [19]

von Stetten et al.

[11] 4,273,865

[45] Jun. 16, 1981

[54] INSOLUBILIZED BIOCHEMICAL MATERIALS

[75] Inventors: Otto von Stetten, Rodgau; Helmut Schmidt, Wuerzburg, both of Fed. Rep. of Germany

[73] Assignee: Byk-Mallinckrodt Chemische Produkte GmbH, Dietzenbach-Steinberg, Fed. Rep. of Germany

[21] Appl. No.: 972,846

[22] Filed: Dec. 26, 1978

[30] Foreign Application Priority Data

Dec. 28, 1977 [DE] Fed. Rep. of Germany ....... 2758507

[51] Int. Cl.³ .................... G01N 33/54; C12N 11/14
[52] U.S. Cl. .................................. 435/7; 260/112 R; 435/28; 435/176; 435/181
[58] Field of Search .................... 435/7, 28, 174, 176, 435/177, 181; 414/12; 260/112 R

[56] References Cited

U.S. PATENT DOCUMENTS

| 3,519,538 | 7/1970 | Messing et al. | 435/176 |
|---|---|---|---|
| 3,715,278 | 2/1973 | Miller | 435/176 |

Primary Examiner—David M. Naff
Attorney, Agent, or Firm—Roy J. Klostermann

[57] ABSTRACT

Stabilized, insolubilized biochemical materials are prepared by covalently bonding a biochemical material such as an antigen, antibody, hormone, or enzyme to a silicic acid heteropolycondensate layer which is applied to a mechanically stable support. The insolubilized biochemical materials are useful as separating agents or adsorbents in radio-immuno assays or affinity chromatography.

27 Claims, No Drawings

INSOLUBILIZED BIOCHEMICAL MATERIALS

This invention relates to stabilized biochemical preparations, preparation and use thereof.

Biochemical materials fixed to solids have been known for some time. This fixing to solids has several advantages. Thus, enzymes, for example, may be stabilized by such fixing and, in this way, retain the activity thereof over prolonged periods, while in solution the activity thereof is lost relatively quickly. In addition, they remain resistant to wider pH ranges and temperature ranges than in solution. The same applied to antigens and antibodies of the type used in immunochemical processes. Another advantage is that it is possible in this way to remove reagents from reaction mixtures simply by filtration, centrifuging or decantation, so that reactions may be controlled with considerable precision with regard to time. In addition, substances may readily be separated by affinity chromatography using fixed materials.

There are several known process for fixing biochemical materials. For example, Catt et al, in an article published in 1967 in Nature 213, 825 (1967), describe a method in which antibodies are adsorbed onto polystyrene tubes. Again in 1967, Axen et al published an article on the chemical binding of peptides and proteins to polysaccharides in Nature 214, 1302 (1967).

In 1970, Kagedal and Akerstrom, writing in Acta Chem Scand. 24, 1601 (1970), described a process for coupling biologically important molecules to polysaccharides in which the molecules are covalently bound. U.S. Pat. No. 3,652,761 describes a process by which antigens and antibodies may be covalently bound via a coupling agent to inorganic supports.

All these processes are attended by certain disadvantages. In the process described by Catt et al, the adsorptively bound material may be desorbed again. In the process described by Axen et al and in the process described by Kagedal and Akerstrom, it is necessary to use toxic substances, such as cyanogen bromide. The process according to U.S. Pat. No. 3,652,761 has to be carried out at high temperatures, for example 625° C., in an oxygen atmosphere, in addition to which the glassware used has to be cleaned using nitric acid.

An object of the present invention is to overcome the disadvantages referred to above an in particular to provide a highly stable biochemical material fixed to a solid. The preparations in question are intended to be able to be readily produced without the use of any toxic substances.

According to the present invention, this object is achieved in that a silicic acid heteropolycondensate layer containing functional groups is applied from an organic solution to mechanically stable supports to which the biochemically interesting materials are fixed by methods known from organic chemistry and biochemistry. The biochemically interesting materials are, for example, serum constituents, proteins, enzymes, antigens, antibodies and haptenes and hormones, particularly albumins, globulins, amino acids and suitably substituted steriods, immunoglobulins, antibodies and hormones being of particular interest.

Accordingly, the present invention relates to stabilised, insolubilised biochemical preparations which are characterised in that biochemical materials, such as antigens, antibodies, hormones, amino acids, haptenes, proteins and enzymes, are covalently bound to a silicic acid heteropolycondensate layer which in turn is applied to a mechanically stable support.

The present invention also relates to a process for the production of these biochemical preparations which is characterised in that a silicic acid heteropolycondensate is produced and applied to a support, after which the biochemical material is coupled thereto, optionally following an after-treatment.

Furthermore, the present invention relates to the use of these stabilised biochemical preparations as agents, for example separating agents or adsorbents, in immunochemical processes, such as radio-immuno assays or affinity chromatography.

The present invention shows the important advantages of being technically particularly simple to materialise and largely independent of the nature and composition of the support used.

The silicic acid heteropolycondensate layer is obtained by the condensation of two or optionally three components, namely:

(a) at least one substituted silane corresponding to the following general formula:

$$SiR_nR''_{(4-n)} \qquad (I)$$

wherein

R represents hydrogen, halogen, alkoxy or $-NR'_2$ (wherein

R' represents hydrogen and/or alkyl); R'' represents alkyl, alkenyl, aryl or aralkyl; and n represents an integer of from 1 to 3;

(b) at least one functional silane corresponding to the following general formula:

$$SiR_n(R'''Y)_{(4-n)} \qquad (II)$$

wherein

R and n are as defined above; R''' represents alkylene, phenylene, alkylphenylene or alkylene-phenylene; and Y represents halogen or an optionally substituted amino, anilino, aldehyde, keto, carboxy, hydroxy, mercapto, cyano, hydroxyphenyl, diazo, carboxylic acid alkyl ester, sulphonic acid ($-SO_3H$) or phosphoric acid ($-PO_3H_2$) group; and, optionally;

(c) at least one hydrolysable silicic acid derivative corresponding to the following general formula:

$$SiR_4 \qquad (III)$$

wherein

R is as defined above, with the proviso that not all the radicals R represent hydrogen.

According to the present invention, therefore, silicic acid heteropolycondensate layers obtained from the above-mentioned components (a) and (b) or (a), (b) and (c) are suitable for application to the support.

It is preferred to use polycondensates obtained by condensation of the following three components:

(a) at least one substituted silane corresponding to the following general formula: $SiR_nR''_{(4-n)}$ wherein R represents chlorine, lower alkoxy, particularly ethoxy or methoxy, or dimethylamine; R'' represents alkyl, particularly methyl or ethyl, aryl, particularly phenyl, or aralkyl, particularly benzyl or tolyl; and n represents an integer of from 1 to 3;

(b) at least one functional silane corresponding to the following general formula: $SiR_n(R'''Y)_{(4-n)}$ wherein R represents chlorine, lower alkoxy, particularly ethoxy or methoxy, or dimethylamino; R''' represents lower alkylene; Y represents optionally substituted amino or anilino, carbonyl, carboxy, diazo or halogen; and n represents an integer of from 1 to 3, particularly 1; and, optionally, (c) at least one hydrolysable silicic acid derivative corresponding to the following general formula: $SiR_4$ wherein R represents chlorine, lower alkoxy, particularly ethoxy or methoxy, or dimethylamino.

Preferably the above mentioned groups contain 1 to 4 carbon atoms.

The term "lower" as used herein (e.g. lower alkyl, lower alkoxy, etc.) is intended to designate groups containing from 1 to 6 carbon atoms.

Suitable starting compounds are, for example, $(EtO)_4Si$, $SiCl_4$, $(MeO)_4Si$, $Si(NH_2)_4$, $(CH_3)_2SiCl_2$, $(CH_3)_2Si(OMe)_2$, $(CH_3)_2Si(OEt)_2$, $(C_6H_5)_2SiCl_2$, $(EtO)_3Si(CH_2)_3NH_2$ and $(EtO)_3Si(CH_2)_3CN$, which may be prepared in accordance with W. Noll's Chemie und Technologie der Silikone, Verlag Chemie, 1968.

According to the present invention, the condensate is produced by mixing the individual components in the absence of moisture, optionally in solution in organic solvents, such as alcohols, particularly lower alcohols, preferably alcohols containing from 1 to 4 carbon atoms, preferably MeOH and EtOH, ketones, particularly alkyl ketones, preferably acetone, ethers, particularly alkyl ethers, preferably diethyl ether and dioxane, amides, preferably dimethyl formamide, and mixtures thereof. A catalyst which is capable of releasing protons or hydroxyl ions or which contains amines is optionally added simultaneously or later.

Condensation of the individual components may be carried out in a single stage or in several component stages, preferably in one or two stages. In the first case, the components are completely condensed in a single stage. In this embodiment of the process according to the present invention, the quantity of water required and, optionally, a catalyst are added to the reaction mixture at the outset. In the second case, the components are first precondensed. Condensation is then completed after the quantity of water required has been added to the precondensate. Condensation may be completed after the precondensate has been applied to the support.

Condensation or precondensation is carried out at temperatures of from $-20°$ to $+130°$ C., preferably from $0°$ to $65°$ C. and, with particular preference, at room temperature. The duration of the condensation reaction amounts to from 1 minute to 24 hours. The duration of the condensation or precondensation reaction influences the mechanical properties of the layers obtained.

The precondensate or the completely condensed product may be applied to and united with the support in the reaction medium. However, it may also be isolated by evaporating off the solvent (optionally in vacuo) and applied to the support at a later stage either as such or in solution in an organic solvent. The stoichiometrically necessary quantity of water is optionally added.

Suitable catalysts for the condensation reaction are acids, particularly volatile acids, preferably hydrochloric acid or acetic acid, water, bases, particularly alkali metal hydroxides or amines, preferably sodium hydroxide or lower alkyl amines. The catalyst is preferably used in an amount of 3%. Where acid catalysts are used, shorter condensation times are preferred.

The precondensation reaction is accompanied, on the one hand, by trans-alkoxylation of the silanes and, on the other hand, by oligomerisation controlled by the reaction conditions selected with simultaneous elimination of ether.

For example, in one embodiment of the process according to the present invention, the dissolved silicic acid heteropolycondensate is applied after the appointed precondensation time to the stable support at elevated temperature either as such or with the assistance of stoichiometric quantities of water. When the solvent is evaporated off, covalent bonds are established between the SiOH groups of the silicic acid heteropolycondensate and the reactive groups of the support. The layers applied are optionally after-treated with water and/or stoved. Biochemically interesting materials may then be coupled to the functional groups of the thus-applied layer by methods known from organic chemistry and biochemistry.

The ratio between the individual components and the condensation conditions determine the properties of the layers obtained. The proportion of hydrolysable silicic acid derivatives determines the surface quality of the layer, for example its specific surface the proportion of substituted silanes (cf. component (a)) determines the adhesion properties and the proportion of functional silanes (cf. component (b)) the number of coupling sites on the surface. The silicic acid heteropolycondensates contain (based on oxides i.e. $SiO_2$ for component (c), e.g. $R''_2SiO$ for component (a), $(R'''Y)_2Si_2O_3$ for component (b)), from 60 to 90%, by weight, preferably from 65 to 85%, by weight, more particularly from 75 to 80%, by weight, of component (a), from 1 to 15%, by weight, preferably from 2 to 10%, by weight, more particularly from 4 to 8%, by weight, of component (b) and from 0 to 30%, by weight, preferably from 5 to 20%, by weight, more particularly from 8 to 15%, by weight, for example from 9 to 12%, by weight, of component (c).

The organic solutions of the condensate have concentrations of from 5 to 40%, more particularly from 10 to 35%, preferably from 25 to 30%. Up to 3% of water or acid is advantageously used as catalyst.

Suitable mechanically stable supports are any strong materials of suitable stability, particularly glass, minerals, for example hydroxyapatite or quartz, ceramics, for example porcelain or white ware, ceramic materials, for example chamotte, metal oxides, for example, aluminium oxide or iron oxide, metals, for example aluminium or iron, wood, paper, carbon, plastics, for example PVC or polyethylene, and organic high polymers, for example cellulose or polysaccharides, preferably glass, for example lens supports, small cylindrical bottles of borosilicate glass (for example having a capacity of 5 ml), fusible glasses (for example $8 \times 70$ mm), ceramics, metal oxides, metals and plastics, for example polypropylene and copolymers of acrylic acid and ethylene.

It has been found to be unnecessary to pre-treat or chemically to clean the supports to be coated, which represents a further simplification over conventional methods. The solution containing the condensate is applied to the support either as such or following the addition of stoichiometric quantities of water. At elevated temperature, generally from $75°$ to $150°$ C., preferably from $100°$ to $120°$ C., the solvent is evaporated off over a period of from 15 to 45 minutes, preferably from 20 to 40 minutes, and the silicone layer is cross-linked and covalently bound to the support.

The following are examples of suitable generally applicable coating processes:

(a) dipping the support to be coated into the solution of the silicic acid heteropolycondensate or into the precondensate and evaporating off the solvent (see above);

(b) spraying the solutions containing the silicic acid heteropolycondensation onto the support to be coated and evaporating off the solvent (see above); and (c) filling container-like supports with solutions containing silicic acid heteropolycondensate and evaporating off the solvent.

The support provided with the silicic acid heteropolycondensate layer is advantageously after-treated with water or steam in order completely to cross-link the silicic acid heteropolycondensate. The water or the steam may have a temperature of from 4° to 150° C., the stability of the layer increasing with the temperature. The after-treatment time may amount to from 2 to 30 minutes. An after-treatment using boiling water for from 10 to 20 minutes has proved to be advantageous. The layer may then be stoved or dried for from 5 to 30 minutes at temperatures of from 100° to 150° C., preferably for from 15 to 25 minutes at from 110° to 130° C. The thickness of the layers does not have any effect upon the serviceability thereof.

Biochemical materials may then be covalently coupled to the silicic acid heteropolycondensate layer provided with functional groups by known methods or organic chemistry and biochemistry described in the literature. Suitable method are described, for example, in U.S. Pat. No. 3,652,761. Depending on the reactivity of the functional groups of the biochemical materials to be coupled and the silicic acid heteropolycondensate layer, the functional groups of the silicic acid heteropolycondensate layer may have to be further modified by known methods of organic chemistry. In general, it is necessary first to derivatise the silicic acid heteropolycondensate layer and then to couple on the required material. Suitable derivatising agents are, for example, amines, carboxylic acids, acid chlorides, thiocarbamates, thiocarbamic acid chloride, diazo compounds, esters or sulphides.

The choice of the modification is dependent upon the conditions required for the following coupling reaction because it is necessary in this respect to work in temperature ranges, pH ranges and media in which irreversible denaturing or loss of activity of the biochemical materials is largely precluded or in which the required characteristics of these materials are not significantly altered. In general, therefore, biochemical materials are coupled at room temperature in aqueous medium at pH values of from 3 to 11. On the other hand, it is important to ensure that the coupling reaction takes place at a sufficient velocity in order not to expose the biochemical materials to non-physiological conditions for too long.

Another factor which has to be taken into consideration is that the activity of fixed biochemical materials frequently depends upon the length of the spacer through which the material is bound to the surface.

With the above-mentioned aspects in mind, it is possible to produce and modify silicic acid heteropolycondensate layers which give optimal results after coating with biochemical material. A layer containing γ-aminopropyl groups may be modified, for example, by treatment with an aqueous, approximately 2.5% glutaraldehyde solution for from 30 to 60 minutes at room temperature. The diazo derivative of the above-mentioned layer may be obtained, for example, by reaction with p-nitrobenzoyl chloride, reduction of the nitro group to form the amine and diazotisation using nitrous acid. In cases where the silicic acid heteropolycondensate layer contains anilino groups by virtue of the use of suitable functional silanes as starting compound, it may be immediately diazotised using nitrous acid. Reaction of amino groups of the silicic acid heteropolycondensate layer with thiophosgene gives the isothiocyano derivative.

The carefully washed derivatised silicic acid heteropolycondensates applied to stable supports are then incubated with the biochemical material in a suitable buffer system, for example acetate (pH 4.0), phosphate (pH 7.0), bicarbonate (pH 9.5) or borate buffer (pH 8.0). During incubation, covalent bonds are established between the silicic acid heteropolycondensate derivatives and the biochemical materials. The incubation times generally amount to from 1 to 72 hours at room temperature. After the excess biochemical material has been removed, the stabilised biochemical materials obtained are either dried in air or in vacuo or are first treated with from 0.5 to 2% solutions of polyvinyl alcohol and then dried. The dry preparations may be stored at temperatures of up to 50° C.

The present invention is illustrated by the following Examples.

EXAMPLE 1

7.5 ml of acetone p.a., 7.5 ml of ethanol p.a. and 0.6 ml of tetraethoxy silane p.a. were mixed and the resulting mixture stored in the absence or air (solution A). Similarly, 7.5 ml of acetone, 7.5 ml of ethanol and 0.35 ml of γ-aminopropyl triethoxy silane were mixed and the resulting mixture stored in the absence of air (solution B). Solution C was obtained by mixing 2.5 ml of acetone, 2.5 ml of ethanol and 10 ml of dimethyl diethoxy silane and was also stored in the absence of air.

For precondensation, volume-equivalent quantities of solutions A, B and C were mixed (solution M) and reacted for 2.5 hours at room temperature in the absence of air.

Quantities of 0.2 ml of the precondensate were then introduced into small glass bottles ("Fiolax" clear glass 40×15 mm), followed by the addition of 15 μl of distilled water. The bottles were then rotated for 30 minutes (5 rpm) at 120° C. in a rotator. The thus-coated bottles were then rinsed for 15 minutes using boiling water and dried at 150° C. 2 ml of 2.5% aqueous glutaraldehyde solution were introduced into the coated bottles which were then left standing for 12 hours at room temperature and then washed with water. Hasen antiserum against triiodothyronine (T3), prepared in accordance with R. D. Hesch and M. Hubner, Acta biol. med. germ 28,861 (1972), in phosphate buffer (pH 7.7) (dilution 1:50,000), was then introduced, followed by incubation for another 12 hours at room temperature. The solution was filtered off under suction, replaced by normal Hasen serum in phosphate buffer (pH 7.7) (dilution 1:25,000) and incubated for 1 hour at room temperature. The solution was removed, followed by washing with water. The bottles coated with triiodothyronine antibody were used in a radioimmunoassay. Quantities of 100 μl of serum standards, containing 0, 50, 100, 200, 400 and 800 ng/100 ml of triiodothyronine, and 1 ml of $^{125}$I-triiodothyronine were then introduced into the individual bottles. After standing for 2 hours at room temperature, the solution was filtered off under suction and the individual bottles measured for residual activity. The bottle containing 0 ng/100 ml of triiodothyronine was found to have a binding level for $^{125}$I-triiodothyronine of Bo/T=34.2%. The residual activity in the bottles containing the standards, based on the residual activity in the O-standard, was as follows: B/Bo=74.7% for 50 ng/100 ml, B/Bo=68.5% for 100 ng/100 ml, B/Bo=52.7% for 200 ng/100 ml, B/Bo=37.0% for 400 ng/100 ml and B/Bo=26.4% for 800 ng/100 ml.

EXAMPLE 2

Solutions A, B, C and M were prepared in the same was as described in Example 1. However, 0.1 ml of 0.1 N HCl was added to 5 ml of solution M, followed by precondensation for 7 minutes at room temperature. For coating, quantities of 0.2 ml were introduced into small glass bottles ("Piolax" clear glass), followed by the addition of 15 μl of water. The layer was applied in the same way as in Example 1.

The thus-treated bottles were then treated for 1 hour using 2.5% glutaraldehyde solution in 0.1 M acetate buffer (pH 4.0), then for 12 hours using T3 antiserum (dilution 1:50,000) in 0.1 M acetate buffer (pH 4.0) and, finally, with Hasen serum (dilution 1:25,000) in acetate buffer (pH 4.0). The function test carried out in the same way as in Example 1 showed a binding level Bo/T of 27%.

EXAMPLE 3

The following starting solutions were prepared by mixing the individual components and were then stored in the absence of moisture:

Solution D: 7.5 ml of acetone, 7.5 ml of ethanol and 1.2 ml of tetraethoxy silane;
Solution E: 7.5 ml of acetone, 7.5 ml of ethanol and 0.7 ml of gamma-aminopropyl triethoxy silane;
Solution C: 2.5 ml of acetone, 2.5 ml of ethanol and 10 ml of dimethyl diethoxy silane.

Volume-equivalent quantities of solutions C, D and E were mixed (solution N) and precondensed for 2 hours at room temperature. Quantities of 0.2 ml of the precondensate were introduced into fusible glass containers (8×70 mm) as manufactured by Messrs. Schott & Gen. The procedure was then as in Example 1.

The containers were then treated for 1 hour using 2.5% aqueous glutaraldehyde solution, washed, incubated for 12 hours at room temperature using T3 antiserum (dilution 1:50,000) in 0.1 M phosphate buffer (pH 7.4), washed, treated for 30 minutes using 1% beef serum albumin (BSA) in 0.1 M phosphate buffer (pH 7.4), washed and tested using with $^{125}$I-T3 in the same way as in Example 1. A binding level Bo/T of 29.5% was obtained.

EXAMPLE 4

0.2 ml of the precondensate of Example 3 were introduced into fusible glass containers (8×70 mm), followed by the addition of 20 μl of water. The coating was applied in the same way as in Example 1. The containers were incubated for 30 minutes at room temperature using 2.5% glutaraldehyde solution, washed, treated for 4 hours at room temperature using T3 antiserum (dilution 1:50,000) in 0.1 M phosphate buffer (pH 7.4), washed, left standing for 30 minutes with 1% BSA in 0.1 M phosphate buffer (pH 7.4), washed and used in a radioimmunoassay in the same way as in Example 1. A binding level Bo/T of 21% was obtained.

EXAMPLE 5

0.1 ml of 0.1 N hydrochloric acid was added to 5 ml of solution N (Example 3), followed by precondensation for 7 minutes at room temperature in the absence of air. 0.2 ml of the precondensate were introduced into small glass bottles ("Fiolax" clear glass, 40×15 mm). The coating was applied in accordance with Example 1.

The bottles were treated for 1 hour at room temperature using 2.5% aqueous glutaraldehyde, washed, incubated for 12 hours at room temperature using T3 antiserum (dilution 1:50,000) in 0.1 M phosphate buffer (pH 7.4), washed, treated for 30 minutes using 0.01% BSA (Behringwerke) in 0.1 M phosphate buffer (pH 7.4), washed and dried in air. The coating was tested in the same way as in Example 1. A binding lever Bo/T of 31% was obtained.

EXAMPLE 6

The glass bottles used in Example 5 were incubated for 2 hours at 60° C. using 10% solutions of tributylamine and p-nitrobenzyl chloride in chloroform, washed with chloroform, boiled for 1 hour with 5% aqueous sodium dithionite solution, washed using water, treated for 10 minutes at 0° C. using a 1% sodium nitrite solution in 4 N hydrochloric acid and thoroughly washed using ice-cold water. T3 antiserum (dilution 1:50,000) was coupled to the diazo groups of the thus-produced silicic acid heteropolycondensate layer by incubation for 12 hours at room temperature in 0.05 M sodium bicarbonate buffer (pH 9.6). This was followed by treatment for 30 minutes using 0.01% BSA in 0.1 M phosphate buffer (pH 7.4). The bottles were tested in the radioimmunoassay according to Example 1. A binding level Bo/T of 47.8% was obtained. The individual standards had B/Bo values of ≙ 79.0% for 50 mg/100 ml, ≙ 60.3% for 100 ng/100 ml, ≙ 37.5% for 200 ng/100 ml, ≙ 25.7% for 400 ng/100 ml and ≙ 14.1% for 800 ng/100 ml.

EXAMPLE 7

The glass bottles of Example 5 were treated using a 1% aqueous terephthalaldehyde solution for 2 hours at from 60° to 80° C. in a water bath, washed using water, incubated for 12 hours at room temperature using T3-antiserum (dilution 1:50,000) in phosphate buffer (pH 6.4), washed, treated for 30 minutes using 0.01% of BSA in 0.1 M phosphate buffer (pH 6.4), rinsed using 0.01 M phosphate buffer (pH 7.4) containing 0.01% of sodium azide and 1% of polyvinyl alcohol (PVA) and dried in vacuo at room temperature. The function test corresponding to Example 1 revealed a binding level Bo/T of 33.9%.

EXAMPLE 8

Glass bottles of Example 5 were treated using a 2.5% aqueous solution of glutaraldehyde for 4 hours at room temperature, washed, incubated for 12 hours using immunoglobulins against hTSH (dilution 1:10,000), prepared in accordance with J. L. Vaitukaitis et al in J. Clin. Endocr. Metab. 33, 1049 (1971), enriched by the method of J. S. Baumstark et al, Arch. Biochem, Biophys. 108, 514 (1964), in 0.1 M phosphate buffer (pH 7.4), washed, treated for 30 minutes using 0.01% of BSA in 0.1 M phosphate buffer (pH 7.4) rinsed using 0.01% of sodium azide and 1% of PVA in 0.01 M phosphate buffer (pH 7.4) and dried.

The glass bottles coated with TSH antibody were treated in the radioimmunoassay using $^{125}$I-TSH. A binding level Bo/T of 56.8% was obtained.

EXAMPLE 9

Glass bottles diazotized in accordance with Example 6 were incubated for 12 hours with immunoglobulins against TSH (dilution 1:10,000) in 0.1 M sodium carbonate buffer (pH 8.4), washed, treated for 30 minutes using 0.01% of RSA in a phosphate buffer (pH 7.4), rinsed using 0.01% of sodium azide and 1% of PVA in 0.01 M phosphate buffer (pH 7.4) and dried. The function test corresponding to Example 8 revealed a binding level Bo/T of 64.4%.

EXAMPLE 10

1.5 ml of diphenyl dichlorosilane were mixed with 3.5 ml of ethanol (solution F). Volume-equivalent quantities of solutions D, E (see Example 3) and F were mixed (solution G), followed by precondensation for 2 hours at room temperature in the absence of air. 0.2 ml of the precondensate were introduced into small glass bottles ("Fiolax" clear glass), followed by the addition of 15 μul of water. The coating was applied in the same way as described in Example 1. The glass bottles diazotised in accordance with Example 6 were incubated for 12 hours using T3 antiserum (dilution 1:50,000) of 0.1 M sodium carbonate buffer (pH 8.4), washed, treated for 30 minutes using 0.01% BSA in phosphate buffer (pH 7.4), rinsed using 0.01% of sodium azide and 1% of PVA in 0.01 M phosphate buffer (pH 7.4) and dried. The function test corresponding to Example 1 produced a bonding Bo/T of 24.3%.

EXAMPLE 11

Volume-equivalent quantities of solutions D, E and F were mixed and precondensed for 24 hours at room temperature in the absence of air. The procedure was then as described in Example 10. The function test produced a binding level Bo/T of 24.1%.

EXAMPLE 12

1 ml of water was added to 5 ml of solution G, followed by precondensation for 2 hours. The high polymer precipitated was filtered off, the solvent was distilled off in a high vacuum and the white powder left behind was stored in the absence of air.

0.1 g of the polymer was dissolved in 50 ml of acetone and 0.1 ml of the resulting acetone solution was introduced into small glass bottles ("Fiolax" clear glass, 40×15 mm). The coating was applied in the same way as described in Example 1. T3 antiserum was coupled to one surface of the bottles in the same way as in Example 10. The function test corresponding to Example 1 produced a binding level Bo/T of 30%.

EXAMPLE 13

1 ml of the acetone solution of the polymer of Example 12 was introduced into 1 ml plastic vessels of a copolymer of polyethylene and acrylic acid (92:8). After 20 seconds, the solution was poured out again and the vessels were dried.

They were then incubated for 30 minutes using 1% glutaraldehyde in 0.1 M phosphate buffer (pH 7.4), washed, treated for 2 hours using T3 antiserum (dilution 1:10,000) in 0.1 M phosphate buffer (pH 7.4), rinsed for 30 minutes using 0.1% of BSA in 0.1 M phosphate buffer (pH 7.4) and dried. The function test corresponding to Example 1 produced a binding level Bo/T of 27%.

EXAMPLE 14

1 ml of the acetone solution of Example 12 was introduced into small glass bottles ("Fiolax" clear glass, 40×15 mm). After 20 seconds, the solution was poured out and the layer adhering to the glass wall was stoved for 15 minutes at 150° C. The procedure was then as in Example 10. The function test corresponding to Example 1 produced a binding level of Bo/T of 30%.

EXAMPLE 15

A 0.01 M solution of $(CH_3O)_3Si-CH_2CH_2CH_2-NH-CO-(C_6H_5)NH_2$ in ethanol/acetone was used instead of solution C in Example 3. Small glass bottles ("Fiolax" clear glass, 40×15 mm) were coated in the same way as described in Example 3.

The glass bottles were treated for 10 minutes at 0° C. using 1% of sodium nitrite in 4 N hydrochloric acid, thoroughly washed and then incubated for 12 hours using T3 antiserum (dilution 1:50,000) in 0.1 M sodium bicarbonate buffer (pH 8.4) washed, left standing for 30 minutes with 0.01% of BSA in 0.1 M phosphate buffer (pH 7.4), rinsed using 0.01% of azide and 1% of PVA in 0.01 M phosphate buffer (pH 7.4) and dried. The function test corresponding to Example 1 produced a binding level Bo/T of 24.8%.

EXAMPLE 16

Glass bottles of Example 6 were treated for 1 hour using 2.5% aqueous glutaraldehyde and washed twice using water. They were then incubated using 6.5 ng of $^{125}$I-triiodothyronine (6, 696, 460 cpm, specific activity 1113 mCi/mg) in 1 ml of 0.1 M phosphate buffer (pH 7.4). 97% of the T3 had been bound after 2 hours, 79% after 3 hours, 81% after 4 hours and 97% after 12 hours. Adsorptively bound hormone was removed by washing for 30 minutes using 0.1 M glycine buffer (pH 2.3). 84% of the hormone, corresponding to 5.5 ng of T3, were covalently bound to the bottles.

EXAMPLE 17

Bottles treated in accordance with Example 16 were incubated using 8 mg of $^{125}$-I-thyroxine (T4) (6, 312, 700 cpm, specific activity 927 mCi/mg). After 2 hours, the binding level had reached 55%, after 4 hours 60% and after 12 hours 69%. After washing, 3, 158, 410 cpm or 56% of the T4 (corresponding to 4.5 mg) remained covalently bound to the bottles.

EXAMPLE 18

Bottles treated in accordance with Example 16 were incubated using 17 mg of $^{125}$I-hTSH (1, 943, 111 cpm, specific activity 117 mCi/mg). After 3 hours, the binding level had reached 10%, after 4 hours 11% and after 12 hours 14%. After washing using glycine buffer, 13% or 2 ng of hTSH remained covalently bound.

EXAMPLE 19

Bottles treated in accordance with Example 16, were incubated using 29 mg of $^{125}$I-beef gamma globulin (BGG) (850,000 cpm, specific activity 28 mCi/mg). After 2 hours, the binding level had reached 5% and after 12 hours 6%. After washing using glycine buffer, 4.5% or 1.3 ng of BGG remained covalently bound.

EXAMPLE 20

Glass bottles diazotised in accordance with Example 6 were incubated using 6.5 ng of $^{125}$I-T3 of Example 16 in 0.1 M bicarbonate buffer (pH 8.0). After 2 hours, the binding level had reached 36%, after 4 hours 41% and after 12 hours 78%. After washing using glycine buffer, 61% for 4 ng of the haptene remained covalently bound.

EXAMPLE 21

The procedure was as in Example 20, except that the bottles were incubated using 8 mg of $^{125}$I-T4 of Example 17. After 2 hours, the binding level had reached 45% and after 12 hours 49%. After washing using glycine buffer, 42% or 3.3 ng of the amino acid T4 remained covalently bound.

EXAMPLE 22

The procedure was as in Example 20, except that the bottles were incubated using 17 mg of $^{125}$I-thyrotropin (hTSH) of Example 18. After 2 hours, the binding level had reached 13% and after 12 hours 24%. After washing using glycine, 17% or 2.8 ng of the proteohormone remained covalently bound to the glass bottles.

EXAMPLE 23

The procedure was as in Example 20, except that the bottles were incubated using 29 ng of $^{125}$I-BBG of Example 19. After 2 hours the binding level had reached 14%, after 3 hours 16% and after 12 hours 20%. After washing using glycine, 19% or 5 ng of the protein remained covalently bound to the glass bottles.

We claim:

1. A stabilized insoluble biochemical composition comprising a biochemical material selected from the group consisting of antigens, antibodies, hormones, amino acids, haptens, and enzymes, covalently bound to a coating of condensed heteropolysilicic acid on a mechanically strong support, the condensed heteropolysilicic acid being a copolymer of the following components:
   (a) at least one substituted silane of the general formula $SiR_nR''_{(4-n)}$, wherein R represents hydrogen, halogen, lower alkoxy or $-NR'_2$, wherein each R' group may be hydrogen or lower alkyl, R'' represents lower alkyl, lower alkenyl, phenyl or phenyl lower alkyl, and n is a whole number in the range of 1–3; said substituted silane expressed as oxide being present in an amount from about 60–90% (w/w);
   (b) at least one functional silane of the general formula $SiR_n(R'''Y)_{(4-n)}$, wherein R has the meaning given above, R''' represents lower alkylene, phenylene, lower alkylphenylene, or lower alkylenephenylene, Y represents halogen, an optionally substituted amino, anilino, aldehyde, keto, carboxy, hydroxy, mercapto, cyano, hydroxyphenyl, carboxylic acid lower alkyl ester, sulfonic acid, or phosphoric acid group; and n is as defined above; said functional silane expressed as oxide being present in an amount from about 1–15% (w/w), and
   (c) at least one hydrolyzable silicic acid derivative of the general formula $SiR_4$, wherein R has the meaning given above, provided that not all the R groups are hydrogen, said silicic acid derivative expressed as oxide being present in an amount up to about 30% (w/w).

2. A composition as defined by claim 1 wherein said hydrolyzable silicic acid derivative is present in an amount of from about 5–20% (w/w).

3. A composition as defined by claim 2 wherein the support is selected from the group consisting of glass, metal oxide, metals, ceramics, minerals and plastics.

4. A composition as defined by claim 3 wherein the biochemical material is selected from the group consisting of the antibodies against the hormones, triidothyronine, thyroxine, estriol, testosterone or thyroid stimulating hormone; the hormones, triodothyronine, thyroxine or human thyroid stimulating hormone bovine gamma globulin; bovine serum albumin; and horseradish peroxidase enzyme.

5. A composition as defined by claim 4 wherein component (c) is a tetraloweralkoxysilane.

6. A composition as defined by claim 4 wherein component (b) is a triloweralkoxyaminoloweralkylsilane or triloweralkoxyaminobenzamidoloweralkylsilane.

7. A composition as defined by claim 4 wherein component (a) is a diloweralkyl-diloweralkoxysilane.

8. A composition as defined by claim 4 wherein component (a) is diphenyldichlorosilane.

9. A composition as defined by claim 4 wherein the support is glass.

10. A method for the preparation of a support as defined by claim 1, comprising attaching to a support said condensed heteropolysilicic acid copolymer of (a), (b) and (c) to form a coating of said copolymer on the support and thereafter covalently binding said biochemical material to the coating.

11. A method as defined by claim 10 wherein the components (a), (b) and (c) before attachment are precondensed by forming a mixture of said components to bring about partial condensation of said components.

12. A method as defined by claim 11 wherein the condensation begun during said precondensation step is completed by attaching said components to said support in the presence of at least the stoichiometric amount of water necessary for hydrolysis.

13. A method as defined by claim 11 wherein the precondensation is carried out in the presence of an acidic or basic catalyst.

14. A method as defined by claim 11 wherein the precondensation is carried out in the presence of water.

15. A method as defined by claim 10 wherein the biochemical material is covalently bound with an aldehyde coupler to said coating of condensed heteropolysilicic acid.

16. A method as defined by claim 10 wherein the biochemical material is bound with diazo groups to the coating.

17. A method as defined by claim 10 wherein the biochemical material is selected from the group consisting of the antibodies against the hormones, triidothyronine, thyroxine, estriol, thyroid stimulating hormone, or testoserone; the hormones triiodothyronine, thyroxine, or human thyroid stimulating hormone; bovine gamma globulin; bovine serum albumin; and horseradish peroxidase enzyme.

18. A method as defined by claim 10 wherein component (c) is a tetraloweralkoxysilane.

19. A method as defined by claim 10 wherein component (b) is a triloweralkoxyaminoloweralkylsilane or triloweralkoxyaminobenzamidoloweralkylsilane.

20. A method as defined by claim 10 wherein component (c) is selected from the group consisting of diloweralkyldiloweralkoxysilanes, and diphenyldichlorosilane.

21. An immunochemical or enzymatical method for determining the concentration of a biochemical member selected from the group consisting of antigens, antibodies, hormones, amino acids, haptens, and enzymes in a measured amount of an aqueous sample wherein said aqueous sample is contacted with (1) an insoluble biochemical material capable of reacting with said member, and (2) a measured amount of tracer labeled member to form after substantial equilibration a two phase system containing a solid phase having a portion of the labeled member and unlabeled member bound to said biochemical material and a liquid phase containing the balance of the unbound labeled member and unlabeled member, the two phases being separated and the concentration of the biochemical member being determined, the improvement comprising using as the insoluble biochemical material, the stabilized insoluble biochemical material of claim 1.

22. In a radioimmunoassay method for determining the concentration of a biochemical member selected from the group consisting of antigens, antibodies, hormones, amino acids, haptens and enzymes in a measured amount of an aqueous sample wherein said aqueous sample is contacted with (1) an insoluble biochemical material capable of reacting with said member and (2) a measured amount of a radioactively labeled member to form after substantial equilibration a two phase system containing a solid phase having a portion of the labeled member and unlabeled member bound to said biochemical material and a liquid phase containing the balance of the unbound labeled member and unlabeled member, the two phases being separated and the radioactivity of at least one of the phases being measured, the value of radioactivity being a function of the concentration of said member in the aqueous sample, the improvement comprising using as the insoluble biochemical material, the stabilized biochemical material of claim 1.

23. A method according to claim 22 wherein said biochemical material is an antibody.

24. A composition as defined by claim 4 wherein the support is a copolymer of polyethylene and acrylic acid.

25. A method as defined by claim 10 wherein the biochemical material is bound with thiophosgene as coupler to the coating.

26. A method as defined by claim 10 wherein the biochemical material is bound with carbodiimide to the coating.

27. A stabilized biochemical composition comprising a biochemical material selected from the group consisting of antigens, antibodies, hormones, amino acids, haptens and enzymes, covalently bound to a coating of condensed heteropolysilicic acid on a mechanically strong support, the condensed heteropolysilicic acid being a copolymer of the following components:

(a) at least one substituted silane of the general formula $SiR_nR''_{(4-n)}$, —wherein R represents hydrogen, halogen, lower alkoxy or $-NR'_2$, wherein each R' group may be hydrogen or lower alkyl, R'' represents lower alkyl, lower alkenyl, phenyl or phenyl lower alkyl, and n is a whole number in the range of 1-3; said substituted silane expressed as oxide being present in an amount from about 60-90% (w/w), and (b) at least one functional silane of the general formula $SiR_n(R'''Y)_{(4-n)}$, wherein R has the meaning given above, R''' represents lower alkylene, phenylene, lower alkenyl phenylene, or lower alkylenephenylene; Y represents halogen, an optionally substituted amino, anilino, aldehyde, keto, carboxy, hydroxy, mercapto, cyano, hydroxyphenyl, carboxylic acid lower alkyl ester, sulfonic acid, or phosphoric acid group; and n is as defined above; said functional silane expressed as oxide being present in an amount from about 1-15% (w/w).

* * * * *